United States Patent [19]

Iles

[11] 4,169,126

[45] * Sep. 25, 1979

[54] TEMPERATURE-RESPONSIVE DEVICE

[75] Inventor: Gerald S. Iles, London, England

[73] Assignee: Johnson, Matthey & Co., Limited, London, England

[*] Notice: The portion of the term of this patent subsequent to Jan. 24, 1995, has been disclaimed.

[21] Appl. No.: 862,427

[22] Filed: Dec. 20, 1977

Related U.S. Application Data

[63] Continuation of Ser. No. 720,394, Sep. 3, 1976, Pat. No. 4,070,157.

[51] Int. Cl.$^2$ .................... G01N 25/30; G01N 25/36
[52] U.S. Cl. ................................. 422/95; 23/232 E; 73/27 R; 422/98
[58] Field of Search ............ 23/254 E, 255 E, 232 E; 73/27 R

[56] References Cited

U.S. PATENT DOCUMENTS

| | | | |
|---|---|---|---|
| 3,478,579 | 11/1969 | Whitmore et al. | 23/254 E |
| 3,567,388 | 3/1971 | Kapff | 23/230 PC |
| 3,586,486 | 6/1971 | Kim et al. | 23/254 E |
| 3,595,621 | 7/1971 | Andreatch | 23/254 E |
| 3,674,436 | 7/1972 | Geul | 23/254 E |
| 3,864,083 | 2/1975 | Green | 23/230 PC |

Primary Examiner—R. E. Serwin
Attorney, Agent, or Firm—Cushman, Darby & Cushman

[57] ABSTRACT

This invention relates to a method and apparatus for detecting changes in the composition of a stream of gas. In particular the method comprises the step of disposing a thermometer in the gas stream, in contact with or downstream of a catalyst so as to detect changes in the temperature of the catalyst or of the gas shortly after it leaves the catalyst, such changes being a function of the amount of gas which reacts under the influence of the catalyst.

1 Claim, 1 Drawing Figure

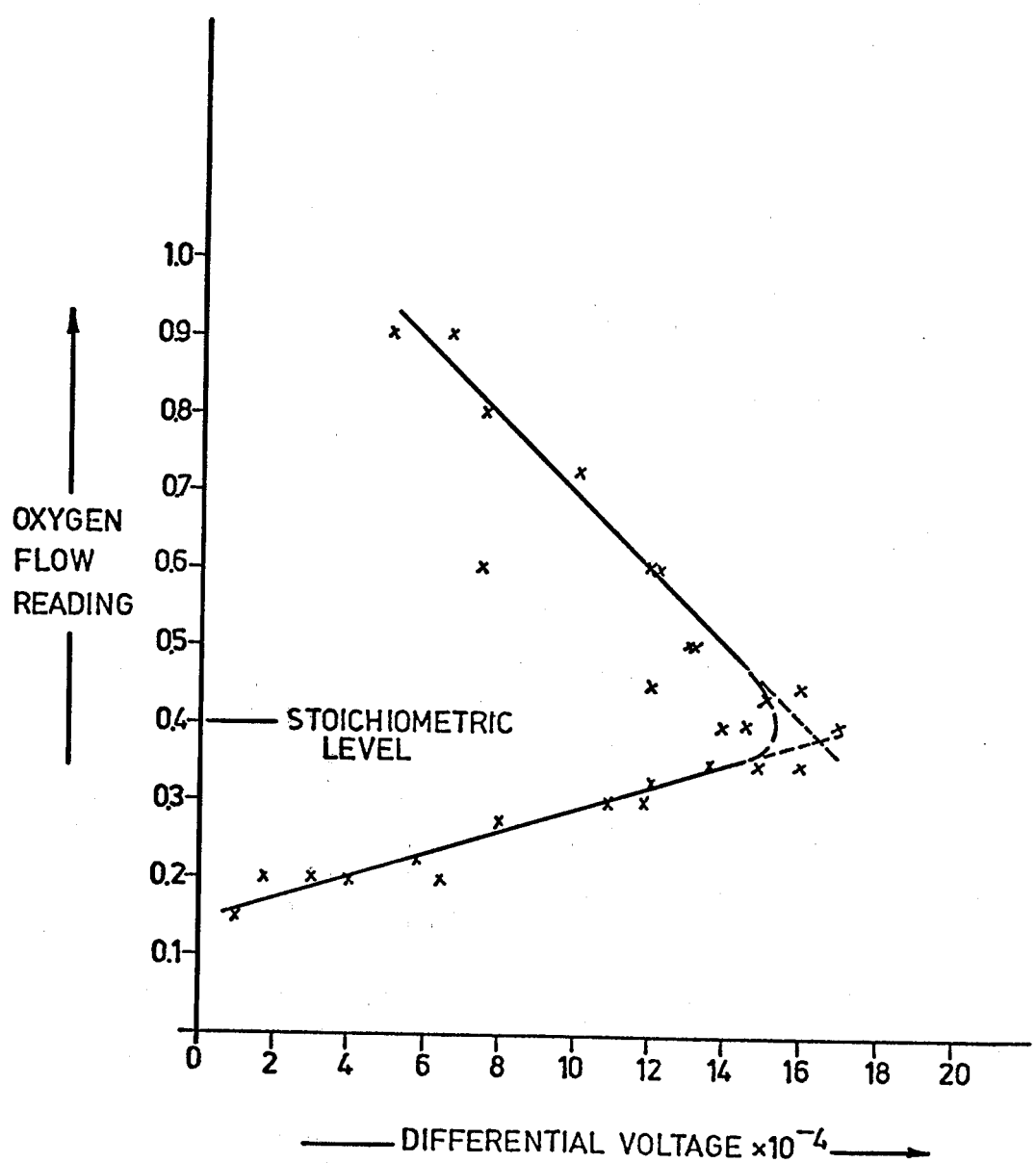

TEMPERATURE-RESPONSIVE DEVICE

This is a continuation of application Ser. No. 720,394, filed Sept. 3, 1976, now U.S. Pat. No. 4,070,157.

This invention relates to the detection of composition changes in a gas stream. In particular, the invention is concerned with the detection of such changes by methods involving monitoring the temperature difference between at least two points separated from each other in the gas stream.

The temperature of a gas stream may be measured by means of a variety of instruments such as thermocouples, resistance thermometers and thermistors. Nowadays all of these may be manufactured to quite small dimensions and all are eminently satisfactory for measuring the temperature of a bulk sample of material which is in thermal equilibrium with its surroundings. However, for fast and accurate measurement of the temperature of a gas stream, which temperature may rapidly fluctuate over a fairly wide range, these instruments possess inherent drawbacks. For instance, thermocouples have only a very small detecting surface and a high thermal mass. Therefore the temperature recorded is not necessarily representative of that of the gas stream and the instrument is sluggish in response. Furthermore, the electrical conductors at the thermoelectric interface impart a "heat-sink" effect to the instrument. Resistance thermometers and thermistors, whilst having in general a larger detecting surface area than thermocouples, still suffer from a high thermal mass.

There has previously been described a composite film resistance thermometer element for the measurement of surface temperatures. This has the advantage of robustness combined with a low thermal mass. As a result of its low thermal mass the element will respond rapidly to sudden changes in temperature whether they are over a wide range or a narrow one and thus a rapidly fluctuating surface temperature may be continuously monitored. In addition, the elements are cheap and simple to produce and the techniques involved may be readily modified to enable automation to be used in their manufacture.

We have now found that composite film resistance thermometer elements are not only suitable for the measurement of rapidly fluctuating surface temperatures but are also suitable for the accurate and rapid detection and measurement of temperature changes in a gas stream. We have also found that such composite film resistance thermometer elements may be used in association with catalyst material for the detection of composition changes in a gas stream provided that the catalyst promotes or changes the rate of one or more reactions between the components of the gas stream and thereby changes the rate of heat generation at the catalyst. In such a case, the composite film resistance thermometer elements are used to detect any resulting temperature changes at the surface of the catalyst or in the gas shortly after it leaves the catalyst. We have still further found that it is preferable to provide a composite film resistance thermometer element to measure the temperature of or to detect temperature change in the gas stream shortly before it reaches the catalyst or in a part of the gas stream close to the catalyst in order that any change in the temperature of the gas or the catalyst as a result of any catalytic reaction may be more readily detected. The invention is not, however, limited to the use of composite film resistance thermometers.

According to one aspect of the invention therefore, a method for the detection of changes in the composition of a stream of gas comprises the steps of disposing a thermometer in the gas stream, in contact with or downstream of a catalyst so as to detect changes in the temperature of the catalyst or of the gas shortly after it leaves the catalyst, such changes being a function of the amount of gas which reacts under the influence of the catalyst.

According to a further aspect of the invention apparatus for detecting changes in the composition of a gas stream comprises a thermometer in contact with or located downstream of a catalyst and arranged to detect changes in the temperature of the catalyst or of the gas shortly after it leaves the catalyst, such changes being a function of the amount of gas which reacts under the influence of the catalyst.

In cases where the temperature of the gas stream at input is likely to vary, it is preferred to dispose a second thermometer upstream of the catalyst and to detect the temperature difference between the two thermometers, the said difference being a function of the amount of gas, which has reacted under the influence of the catalyst.

The thermometer may be an electric resistance thermometer and preferably is a composite film resistance thermometer. The thermometer preferably includes an electrically resistive element suitable for use as the temperature sensitive element of a resistance thermometer and comprising a layer of vitreous material loaded with electrically conducting particles and secured to a substrate of electrically non-conducting material.

One especially useful application of the invention is in the detection of composition changes in the exhaust gas stream from an internal combustion engine when the exhaust system of such an engine is provided with a catalytic converter for the oxidation of hydrocarbons and carbon monoxide or for the reduction of nitrogen oxides. In a typical arrangement one element is mounted as a probe in the exhaust gas stream immediately upstream from, but not in contact with, a catalyst, and a further element of similar resistance value as the first is mounted in a similar way but immediately downstream of, but not in contact with, the catalyst. The elements are electrically connected in series and supplied with a constant current. Further electrical connections are taken from each element so that the potential developed across each element can be monitored. Under constant current conditions the potential developed in each element is proportional to the temperature. The two elements therefore act to detect and measure temperature changes in the exhaust gas stream immediately upstream and down stream of the catalyst. Under any given set of normal engine operating conditions the elements will record steady temperatures; if the catalytic reaction is exothermic then the downstream element will record a higher temperature than the upstream element and in the case of an endothermic reaction the upstream element will record the higher temperatures. Conduction heat losses through the catalyst may have some effect in reducing the temperature recorded by the downstream element compared to that of the upstream element, whether the catalytic reaction is exothermic or endothermic. However, under abnormal engine operating conditions such as misfiring due to, for instance, faulty ignition equipment or valve gear, the hydrocarbon content of the exhaust gas stream increases significantly. The excess hydrocarbons are burnt at the catalyst and the elements immediately register a rise in the temperature of the gas stream both upstream and downstream from the catalyst. The downstream element records a higher temperature rise than does the upstream element such that the difference between the temperatures recorded by the elements is substantially greater than that appertaining to normal engine operating conditions. Under extremely abnormal operating conditions such as those evidenced by a very high hydrocarbon content in the exhaust gas stream, spontaneous ignition upstream from the catalyst can occur. This may be described as "flare-out" and is detected by the elements as a sudden increase in the temperature of the gas stream upstream from the catalyst and a simultaneous decrease in the downstream temperature.

Abnormal engine operating conditions, which cause flare-out or combustion of excess hydrocarbons at the catalyst, ultimately lead to failure of the catalyst support through overheating and, in the case of flare-out, excess pressure. However, the elements, acting in association with the catalyst as described, detect these abnormal conditions and can be made to operate a warning signal or some other alleviative device.

In a further application of the invention it may be used as a mixture controller for internal combustion engines using fuel injection. In this arrangement, one of the composite film resistance thermometer elements is coated with a catalyst material on the glazed surface lying immediately over the resistive track. The other element is positioned in a back to back configuration with the coated element. Thus the catalyst coating of the one element and the resistive track of the other element both face to the outside. The elements are mounted in a holder and electrically connected as before, that is to say, in series and supplied with a constant current, further connections being taken from each element to monitor the potential developed. The assembly is inserted into the exhaust gas stream at some convenient location downstream from the engine exhaust manifold.

The uncoated element will measure the temperature of the exhaust gas stream. The catalyst layer will catalyse the oxidation of carbon monoxide and hydrocarbons and the element supporting the catalyst will record the temperature of the catalyst surface. The instrument will thus record a temperature differential which will vary with varying exhaust gas composition.

The FIGURE shown in the drawing is a plot of oxygen flow rate versus voltage difference between the elements.

It has been determined experimentally, using the arrangement described above in a simulated exhaust gas stream composed of nitrogen and carbon monoxide at constant flow rates and oxygen at a variable flow-rate, that plotting varying oxygen flow rates against the voltage differences between the elements, such voltage differences being proportional to the temperature differences between the elements, gives a quadratic curve with a maximum, bounded by steep gradients, in the region of the stoichiometric carbon monoxide to oxygen composition. This is illustrated in the FIGURE. It follows from this that the instrument may be associated with electronic circuitry to enable the voltage difference to be kept at a maximum, by monitoring and adjusting the fuel-to-air ratio to maintain it at the stoichiometric level. A suitable electronic modification would be to energise the instrument with an alternating current from a solid state oscillator. This would allow the provision of an appropriate signal to a fuel mixture control device, according to whether the arrangement indicates a rich or lean mixture.

A heating device may be incorporated into the arrangement to enable it to be used even under "cold-engine" conditions, before the exhaust gases have heated the appropriate element sufficiently to allow catalytic oxidation to proceed.

In yet another application of the invention, an arrangement, substantially as described above with reference to the mixture control aspect, may be used to monitor the performance of an exhaust gas conversion catalyst. The elements are placed in an exhaust gas stream downstream from a catalytic conversion unit. Should the catalytic converter cease to function for any reason, unconverted flammable gases will reach the instrument where combustion will take place on the catalytic coating of the coated element. The temperature of the catalytic surface is measured in terms of electrical resistance by this element; the uncoated element measures the ambient temperature of the exhaust stream in terms of electrical resistance and a voltage difference is obtained, which may be used to activate control or warning devices.

The invention is not necessarily confined to internal combustion engine exhaust systems in automobiles, nor even to an internal combustion engine exhaust system in any other particular application. The invention may be used in a variety of domestic and industrial situations wherever it is required to detect changes in the composition of a gas stream. One such use of the apparatus according to the invention is as a detector in a gas chromatography instrument.

It is possible to vary the sensitivity of the apparatus according to the invention by providing a plurality of terminals connected respectively to the resistive track at intervals along the length of the track so that a particular resistance value for a given current and operating temperature range may be preselected.

What we claim is:

1. Apparatus for detecting changes in the composition of a stream of gas resulting from contact with a catalyst, said apparatus comprising first and second composite film electrical resistance thermometers which are connected in series and means for monitoring the voltage difference between said thermometers, said first thermometer including a coating of said catalyst and the two thermometers being arranged in side-by-side relationship in a holder such that at least the resistive track of the second thermometer or the catalyst coating of the first mentioned thermometer is exposed to said gas stream.

* * * * *